United States Patent [19]
Por

[11] Patent Number: 6,015,094
[45] Date of Patent: Jan. 18, 2000

[54] VEHICLE PERFUME DISPENSER

[76] Inventor: Sze Pik Por, 6 General Lim St., San Antonio Village, Pasig City, Philippines, 16000

[21] Appl. No.: 08/974,373

[22] Filed: Nov. 19, 1997

[30] Foreign Application Priority Data

May 9, 1997 [PH] Philippines ..................... S.N.I.-56394

[51] Int. Cl.⁷ ....................................................... A24F 5/00
[52] U.S. Cl. ................................................................ 239/44
[58] Field of Search ........................... 239/34, 44; 73/514

[56] References Cited

U.S. PATENT DOCUMENTS

| | | | |
|---|---|---|---|
| 3,442,197 | 5/1969 | Gobang | 239/44 |
| 4,913,034 | 4/1990 | Ripple et al. | 239/34 |
| 5,282,571 | 2/1994 | Smith et al. | 239/34 |
| 5,428,996 | 7/1995 | Abbink et al. | 73/514 |
| 5,549,247 | 8/1996 | Rossman et al. | 239/34 |

FOREIGN PATENT DOCUMENTS 1125225  9/1958  Germany .................................. 239/34

*Primary Examiner*—Kevin Weldon
*Attorney, Agent, or Firm*—Christensen O'Connor Johnson and Kindness PLLC

[57] ABSTRACT

A vehicle perfume dispenser for mounting on the dashboard of a vehicle. The dispenser is operative to release perfume during the acceleration or deceleration of the vehicle. The vehicle perfume dispenser includes a lower case member provided with a perfume cartridge receptacle disposed at the front of the lower case member. The dispenser also includes a rear upper hollow case member mounted at the upper rear portion of the lower hollow case member and having at least a pair of longitudinally disposed slots. The dispenser also includes a see-sawing rectangular member adapted to be pivotably mounted on the lower casing and further having a counterweight. The rectangular member has a rotatively secured equilibrium adjusting apparatus for adjusting the rotation of the rectangular member relative to the lower casing.

5 Claims, 3 Drawing Sheets

6,015,094

VEHICLE PERFUME DISPENSER

FIELD OF THE INVENTION

The present invention relates generally to perfume dispensers. But more particularly to a perfume dispenser for cars or the like whereby, perfume smell is given off in response to the forward and backward motion of the car.

BACKGROUND OF THE INVENTION

Car air fresheners or deodorizers being sold in the market include tin cans, cardboard, and those in liquid form. These fresheners are provided with an opening that gives off smell continuously. These kinds of air fresheners or deodorizers have the drawback that the smell is continuously dispensed which renders our sense of smell immune to it as if one does not smell the perfume at all.

SUMMARY OF THE INVENTION

It is therefore an object of the invention to remedy the aforementioned drawbacks of the prior art by providing a novel vehicle perfume dispenser that does not tire our sense of smell, since the subject perfume dispenser provides only an intermittent flow of perfume when the vehicle is in motion and automatically closes when the vehicle stops. This therefore provides a longer use of perfume as compared with the existing ordinary car fresheners sold in the market.

Another object of this invention is to provide a perfume dispenser having an oscillating means that pushes the flapping cover of the perfume dispenser to release the perfume.

Still another object of the present invention is also to provide a perfume dispenser having a tilting clearance adjustable means playing a significant dual role of adjusting the tilting clearance and also to achieve the needed adjustment, to match the degree of inclination of the perfume dispenser with respect to the position of the car's dashboard whereby the desired intermittent release of the perfume scent inside the room area of the car is realized A further object of invention is to provide a perfume dispenser having an equilibrium adjusting means disposed at the top portion of the flapping cover to determine the desired easy opening or closing of said flapping cover.

Yet an object of this invention is to provide a perfume dispenser having a very simple construction that can be manufactured using a simple equipment, whereby the resulting product is not just novel but ornamental as well.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
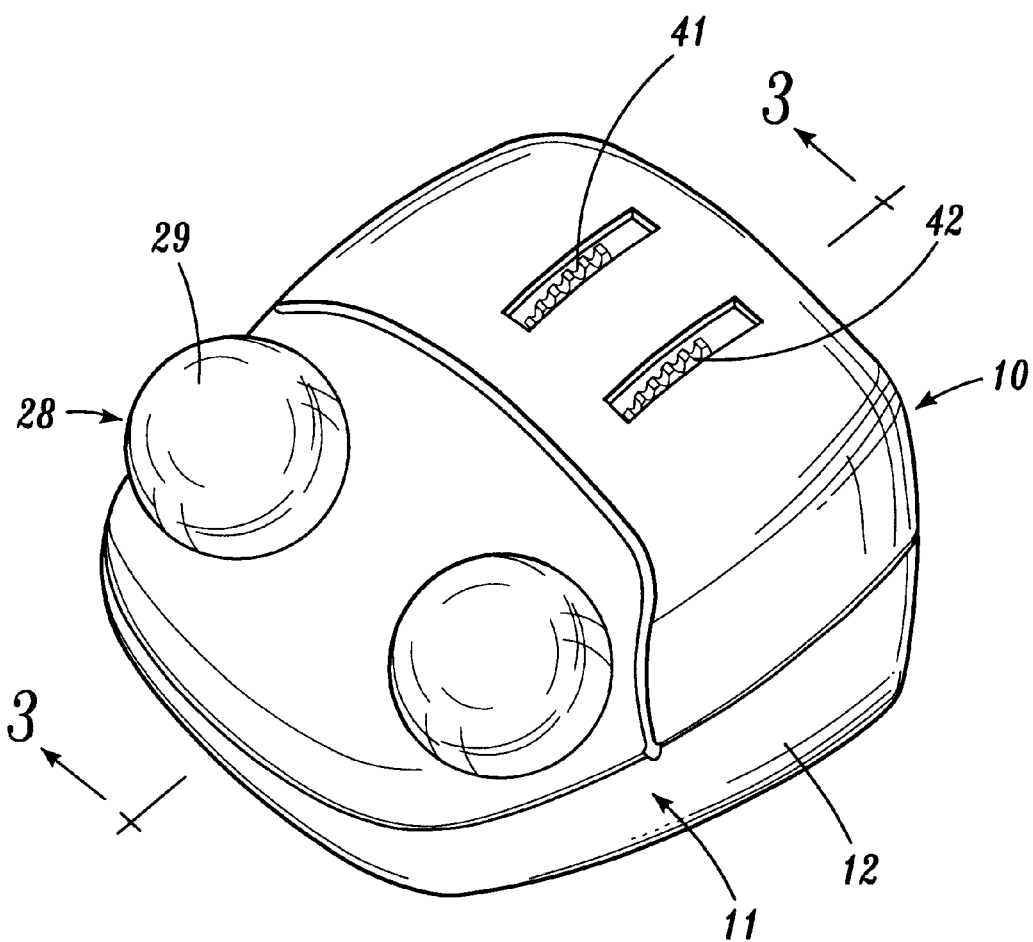
FIG. 1 is a perspective view of the present invention for a perfume dispenser.

Referring now to the several views of FIGURES, there is shown an invention for a vehicle perfume dispenser generally designated as reference numeral 10. The perfume dispenser 10 is used to deodorize the inside room area of a car or the like whereby, the release of perfume is responsive to the forward and backward motion of a car.

The perfume dispenser 10 comprises a casing 11 defined by a lower hollow case member 12 and an upper rear hollow case member 13 adapted to be sealed or adhered at the upper rear portion of said lower hollow case member 12. The rear upper hollow case member 13 is provided with a pair of longitudinally disposed slots W. At the forward portion of said rear upper hollow case member 13 is a scent outlet 14 through which the perfume scent is released.

The outlet 14 exposes the perfume cartridge receptacle 15 disposed within the forward portion of said lower hollow case member 12. The rear portion of said lower hollow case member 12 is further provided with a pair of oppositely disposed pin holder casings X having apertures Y adapted to receive thereon screws Z. Said outlet 14 is provided with a flapping cover means 16 that is made adjustable for easy opening or closing whenever said dispenser 10 is subjected to forward or backward motion.

At the upper rear portion of said cartridge receptacle 15 is an actuating mechanism 17 that drives the opening and closing of the flapping cover means 16, so as to release the perfume scent from the perfume cartridge receptacle 15 intermittently.

The actuating mechanism 17 consists of a see-sawing rectangular member 18 having a rectangular slot U and further having a pair of opposed pins 19 rotatively held in the respective pin holders 20 screwably mounted by screw Z, through apertures Y on said pin holder casings X provided on said lower hollow case member 12. The front side of said see-sawing rectangular member 18 has a plane portion 38 where the flapping cover means 16 is screwably connected thereto. To attain equilibrium balance, the rear lower portion of said rectangular member 18 is provided with a counterweight 23. The pair of opposed pins 19 protrudes outwardly and disposed approximately on both sides of said rectangular member 18 where the two "Centers of Balance" 21 are located. It is to be noted from FIG. 2 that the location of said "Centers of Balance" 21 cover all the weight provided by counterweight 23, flapping cover means 16, equilibrium adjusting means 28, and the rectangular member 18 per se.

The upper front portion of said flapping cover means 16 is provided with a pair of equilibrium adjusting means 28, being defined by a pair of circular rotating knob 29 screwably connected therein and each having center pins 30 and a protruding socket member 31. The flapping cover means 16 is provided with an opposed pair of semicircular slots 32, adjusted to receive thereon said socket member 31 and the protruding lug members 33, provided holes 34 adapted rotatively held thereon said center pins 30. The socket members 31 are connected to said flapping cover means 16 by means of the weight adjusting screws 35, springs 36 and washers 37. The springs 36 provide the needed frictional force between the equilibrium adjusting means 28 and flapping cover means 16 to avoid the unwanted movement of the equilibrium adjusting means 28.

Supporting the bottom portion of said flapping cover means 16 is a support plane portion 38 screwably connected thereon by means of screws 39 which pass through the slots 40 fixed at the bottom portion of said holes 34 which are fixed together by said screws 39.

To provide movement to said rectangular member 18, an oscillating means 24 is defined by an oscillating weight 25 disposed below said rectangular member 18. The oscillating weight 25 is provided with a pair of connecting rods 26 projecting upwardly fixed to a transverse shaft 27. The oppose pin ends 22 of said transverse shaft 27 are rotatively held in the said pin holders 20. To initiate movement of said rectangular member 18, a gear-like shaped plate tilting member 42 projects upwardly from said transverse shaft 27. The transverse shaft 27 is actuated by means of the said oscillating weight 25 due to the forward and backward motions of the car thereby, said tilting member 42 pushes down the rear portion 47 of said rectangular member 18 when subjected to a forward and backward motions, respectively.

Figure 2:
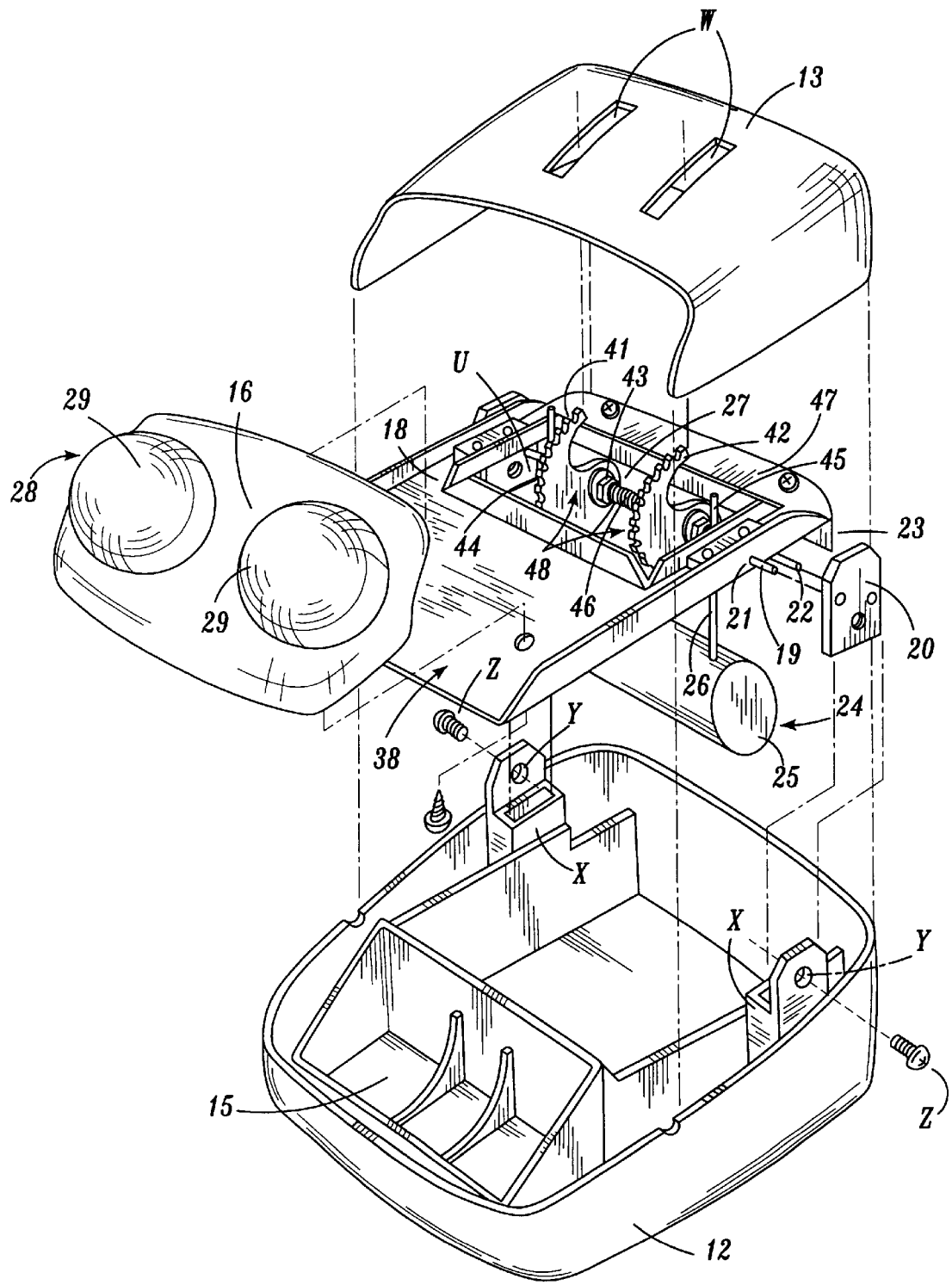
FIG. 2 is an exploded view of said dispenser showing the adjusting means thereof.
Figure 3:
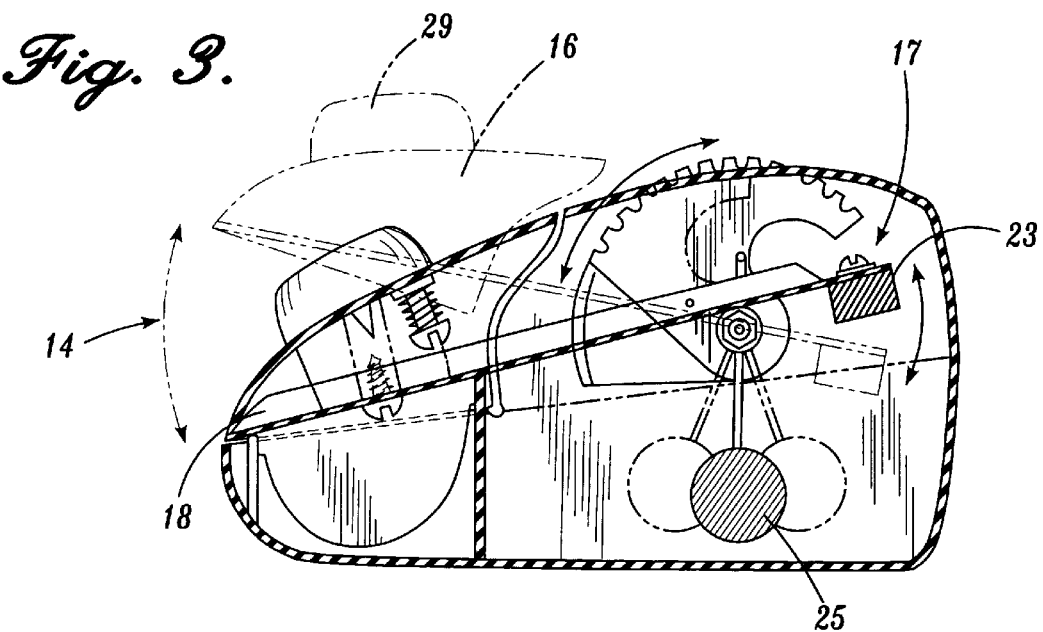
FIG. 3 is a cross-sectional view taken along line 3—3 of FIG. 1.
Figure 4:
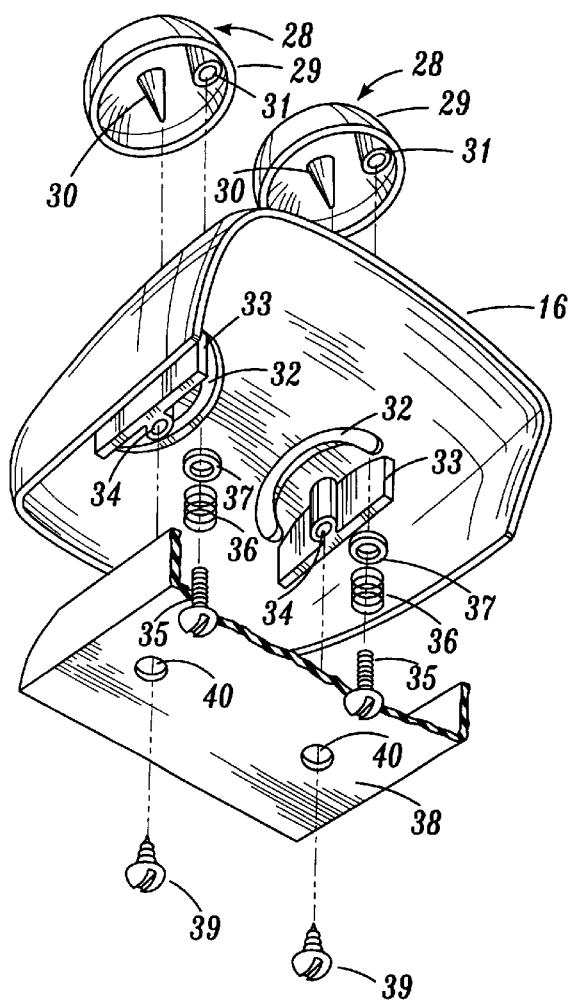
FIG. 4 is an exploded view of the upper front cover of the same.

As shown in FIG. 2, said dispenser 10 is provided with a tilting clearance adjustable means 48 associated with oscillating weight 25, for adjusting the intermittent opening of said flapping cover means 16, with respect to the position of said vehicle perfume dispenser 10, in so far as the degree of inclination of the car's dashboard (not shown) top of the aircon window is concerned. The oscillating weight 25 provides the necessary weight for the connecting rods to be approximately in vertical form when the perfume dispenser is not in motion, and provides the necessary tilting force when the same is in motion. The tilting clearance adjustable means 48 includes a pair of oppositely disposed gear-like shaped plate stopper member 41 and tilting member 42 mounted on said transverse shaft 27, and project upwardly through said rectangular slot U and said longitudinally disposed slots W so that it could be made freely movable and for easy adjustment of the needed tilting clearance. The stopper member 41 is made to be fixed on said transverse shaft 27 by means of nuts 43 and 44 provided on both sides, while the tilting member 42 is made pivotally held on said shaft 27 by means of only one nut 45 provided thereon and a spring 46 is disposed in between said plate member 41, 42. To enable said tilting member 42 for the needed clearance adjustment against the rear portion 47 of said rectangular member 18. Said spring 46 provides the needed frictional force between the said transverse shaft 27 and tilting member 42, to avoid the unwanted movement between said member 42 and transverse shaft 27.

The adjustment of tilting clearance adjustable means 48 is made possible by holding the stopper member 41 and simultaneously adjusting the distance between the tilting member 42 with respect to said rear portion 47 by moving said tilting member 42 in a back and forth movement. To achieve the desired clearance between the tilting member 42 and rear portion 47, the significant dual role of the tilting clearance adjustable means 48 is therefore adjusting the tilting clearance and also to achieve the needed adjustment to match the degree of inclination of the perfume dispenser with respect to the position of the car's dashboard whereby the desired intermittent release of perfume scent inside the room area of the car is realized. Such novel features are not inherent insofar as the prior arts of existing perfume dispensers are concerned.

Should the occupant of the vehicle wish to adjust the easy opening and closing of the flapping cover means 16, the equilibrium adjusting means 28 are rotated within the area provided by the semi-circular slot 32, which likewise move the weight adjusting screw 35 in the same direction. The combined weight of the socket member 31, weight adjusting screw 35, springs 36 and washers 37 provide the needed equilibrium adjusting weight, such that when said weight adjusting screws 35 are placed at the rear side portion of the equilibrium adjusting means 28, the said combined weight is therefore transferred to the rear portion of said flapping cover means 16 causing the same to open or vice-versa.

In operation, the vehicle perfume dispenser is first placed on the car's dashboard top of a vent, (the nearer the better), then adjust the tilting clearance adjustable means 48 to match the degree of inclination of the car's dashboard and at the same time in doing so, the desired tilting clearance is achieved. Adjust the equilibrium adjusting means 28 just enough to move the flapping cover means 16 to close lightly. When the vehicle moves forward or backward, the oscillating means 24 moves counter to the direction of the car due to the pull back force applied to the oscillating weight 25. The swinging motion of said oscillating means 24 causes the tilting member 42 to push down the rear portion 47 thereby lifting the flapping cover means 16 and releasing the perfume scent inside the room area of the car. As the oscillating means 24 swings to the other side, the tilting member 42 releases the said rear portion 47, said see-sawing rectangular member 18 then returns to its original position causing the flapping cover means 16 to close.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A vehicle perfume dispenser adapted to be placed on top of a vehicle dashboard comprising:
   a bottom case member having a perfume cartridge receptacle disposed at a front portion of said bottom case member and at least one pair of pin holder casings secured thereto;
   a rear upper cover mounted at an upper rear portion of said bottom case member and having at least a pair of longitudinally disposed slots;
   a see-sawing member adapted to be pivotally mounted on said bottom case member and having a rectangular slot and a counterweight;
   a flapping cover secured at a front portion of said see-sawing member and having at least one equilibrium adjusting means; and
   oscillating means rotatively held within said rectangular slot and having a tilting clearance adjustment means that includes at least one stopper member and one tilting member projecting upwardly through said rectangular slot.

2. The vehicle perfume dispenser of claim 1 wherein said equilibrium adjusting means is a rotating knob connected to said flapping cover by means of a weight adjusting screw to provide adjustable equilibrium weight and provide frictional force between said equilibrium adjusting means and said flapping cover to avoid the unwanted movement of the equilibrium adjusting means.

3. The vehicle perfume dispenser of claim 1, wherein said oscillating means is an oscillating weight provided with a pair of connecting rods projecting upwardly and fixed to a transverse shaft.

4. The vehicle perfume dispenser of claim 1, wherein said see-sawing rectangular member is provided with a front plane portion to which said flapping cover is connected, a counterweight fixed at the rear lower portion thereof to provide equilibrium balance, and a pair of opposed pins rotatively held in the pinholder inside said casing.

5. The vehicle perfume dispenser of claim 3, wherein said tilting clearance adjustment means consists of at least one stopper member, one tilting member that provides adjustment with respect to the degree of inclination of the perfume dispenser, and a spring disposed on said transverse shaft that provides frictional force between said transverse shaft and said tilting member to avoid the unwanted movement between said tilting member and said transverse shaft.

* * * * *